United States Patent [19]

Shoher et al.

[11] 4,426,404
[45] Jan. 17, 1984

[54] PREPARATION OF AN INTERMEDIATE LAYER BETWEEN A HIGH-MELTING DENTAL METAL ALLOY AND DENTAL PORCELAIN

[75] Inventors: Itzhak Shoher; Aaron Whiteman, both of Tel Aviv, Israel

[73] Assignee: Etablissement Dentair Ivoclar, Schaan, Liechtenstein

[21] Appl. No.: 324,901

[22] Filed: Nov. 25, 1981

[30] Foreign Application Priority Data

Dec. 9, 1980 [DE] Fed. Rep. of Germany ....... 3046334

[51] Int. Cl.$^3$ .............................................. A61C 13/00
[52] U.S. Cl. ......................................... 427/2; 106/35; 148/24; 228/209; 427/226; 427/227; 427/229; 427/404; 433/200; 433/201; 433/223
[58] Field of Search .................. 106/35; 428/473, 472, 428/672, ; 520/442, 444; 148/24; 427/2, 229, 226, 227, 343, 404, 405; 228/209

[56] References Cited

U.S. PATENT DOCUMENTS

| | | | |
|---|---|---|---|
| 3,121,629 | 2/1964 | Mann | 420/144 |
| 4,010,048 | 3/1977 | Tesk et al. | 148/24 |
| 4,077,560 | 3/1978 | Sung | 228/220 |
| 4,181,757 | 1/1980 | Youdelis | 427/229 |

*Primary Examiner*—Theodore Morris
*Attorney, Agent, or Firm*—Sprung, Horn, Kramer & Woods

[57] ABSTRACT

A process for producing and intermediate layer between a high-melting dental alloy and a dental porcelain which comprises applying to said high-melting dental metal alloy a composition comprising.
 (a) at least a metal or a metal alloy which is thermally stable at a temperature of at least 800° C.;
 (b) gold or a gold compound which decomposes to metallic gold, or a gold alloy;
 (c) at least one flux; and
 (d) aluminum and/or solver or an aluminum-silver alloy or a silver compound which decomposes two metallic silver, in a liquid vehicle (A) in which component (c) is at least partially soluble, drying the so-treated high-melting dental metal alloy and sintering said composition and thereafter treating the so-sintered composition with a liquid (B) in which the non-metallic components of said composition are at least partially soluble.

11 Claims, No Drawings

PREPARATION OF AN INTERMEDIATE LAYER BETWEEN A HIGH-MELTING DENTAL METAL ALLOY AND DENTAL PORCELAIN

BACKGROUND OF THE INVENTION

1. Field of the Invention

This invention relates to a sinterable base composition for preparing an intermediate layer between dental porcelain and a high-melting dental metal alloy, especially a nonprecious metal alloy, as well as to a method of preparing such an intermediate layer.

2. Discussion of Prior Art

Sinterable base compositions are used in denistry in order to improve the adhesion between a metal coating, usually of a nonprecious metal alloy, and a dental porcelain which is fused on afterwards. In the making of dentures, especially of crowns and bridgework, dental porcelain is applied to a metal substructure, a crown for example, which must be especially pretreated and cleaned, and it is fired on in layers at high temperatures, so as to achieve an aesthetically pleasing denture.

It has been found, however, that the adherence of the dental porcelain to the metal is in many cases unsatisfactory and depends to a high degree on the ability of the dental technician. This is the case especially when the nonprecious metal alloy is one of the alloys now on the market which are made on a basis of nickel, chromium and/or cobalt, which may also contain other additives such as molybdenum, aluminum, silicon, manganese, iron etc. Nonprecious metal alloys are today increasingly used for reasons of cost, and they are sufficiently described in the literature.

In order to improve the adhesion between metal and dental porcelain, a variety of binding agents have already been proposed. According to German Offenlegungsschrift No. 25 25 274, gold powder, dental porcelain, zirconium dioxide and liquid fluxes are used in certain proportions as binding agents between dental porcelain and metal. The liquid flux also contains vehicle substances, such as glycerol or alcohol. It can consist of boron oxide or the salts thereof, such as sodium borate, or the oxides of the light elements, such as lithium oxide, sodium oxide etc. During firing, the flux, together with the dental porcelain and the oxides, forms on the alloy a tough intermediate layer of oxides of low solubility, to which the dental porcelain adheres strongly during the subsequent firing.

A mixture of boron and aluminum together with an organic vehicle component is known as an adhesive composition from German Offenlegungsschrift No. 26 12 554. According to this disclosure, an uniform layer of boron and aluminum dispersed in petroleum jelly, for example, is applied to a cleaned metal substrate, and then coated metal is rapidly raised to a high temperature and the binding agent is fired on. The coated surface is cleansed after cooling, and the dental porcelain can be fired on in the conventional manner.

German Offenlegungsschrift No. 26 26 092 discloses a binding agent containing an aluminum powder, a glass powder and an organic vehicle. The vehicle component produces a reducing atmosphere during the sintering. The glass is a mixture of noncrystalline oxides which include $SiO_2$, $Al_2O_3$, $Na_2O$, $CaO$, $MgO$, $K_2O$, $SnO_2$, $Li_2O$, $B_2O_3$, $Fe_2O_3$ and $BaO$.

Also pertaining to the state of the art German Offenlegungsschrift No. 26 32 871 are methods in which a mixture of Ni-Cr-Al and ceramic ($Al_2O_2$, $ZrO_2$, $TiO_2$) is deposited from a vapor on the metal substrate.

Also the production of an intermediate layer consisting of gold, porcelain and $ZrO_2$ and a flux is known from U.S. Pat. No. 4,181,757.

However, none of the above-described adhesives or binding agents is as yet satisfactory with regard to the improvement of adhesion between the metal substrate and the dental porcelain. Some of the processes are complex and expensive, and some of the binding agents improve only the chemical bond between metal and porcelain.

SUMMARY OF THE INVENTION

It is an object of this invention, therefore, to provide a base composition which, after being sintered onto the metal substrate, improves the adhesion between a high-melting dental metal alloy, especially a nonprecious metal alloy, and dental porcelain, not merely by chemical bonding mechanisms but also by means of mechanical retention.

This object is achieved in accordance with the invention by a sinterable base composition of the type defined above, comprising the following components:

a at least one high-melting, especially nonprecious metal or a high-melting metal alloy, especially a dental metal or a dental mental alloy;

b gold or a gold compound which decomposes to metallic gold, or a gold alloy;

c at least one flux; and d aluminum and/or silver or an aluminum-silver alloy, or a silver compound which decomposes to metallic silver.

The base composition of the invention may additionally contain (e) silica and/or (f) zirconium dioxide.

The term, "high-melting" metals or metal alloys, as used herein, is to be understood to mean metals and alloys which are thermally stable at the temperatures at which dental procelains or glazes are commonly sintered in place, e.g., 800° to 1200° C. The firing temperatures of dental porcelain are commonly within this temperature range. The high-melting metals or alloys are sold in a great variety of compositions as commercial products, a distinction being made between noble metals and nonprecious metals and the corresponding alloys. Examples of noble metals are gold and the metals of the platinum group. Examples of nonprecious metals are nickel, cobalt, chromium, molybdenum, tungsten, manganese, tantalum, titanium and zirconium.

The gold and silver compounds which decompose to metallic gold or silver, and which are usable in accordance with the invention, can be the gold or silver halides. The silver halides decompose at or below the common sintering temperatures. The gold halides decompose at still lower temperatures. Another thermally decomposable silver compound is, for example, silver oxide.

If the base composition of the invention is sintered onto a high-melting dental metal alloy, for example onto a metal substrate such as a crown, bridge or the like, one obtains after further treatment an intermediate layer onto which the dental porcelain is fired, thereby obtaining a denture which can be subjected to substantially greater stress than if the base composition of the invention were not to be used. In particular, when the base composition of the invention is used, the danger of the breaking off of dental porcelain such as constantly occurs in the event of high unforeseen chewing stresses, is reduced.

The method of preparing an intermediate layer between dental porcelain and a high-melting dental metal alloy, especially a nonprecious metal alloy, is likewise subject matter of the present invention. This method is characterized by the fact that a base composition of the invention is mixed with a liquid vehicle (A) in which the flux (component c) is at least partially soluble, the mixture is applied to the high-melting dental metal alloy and dried and sintered in place, and the sintered base composition is treated with another liquid (B) in which the nonmetallic components of the base composition are at least partially soluble.

Preferably, at least the components a, b and d, plus components e and f, if used, are contained in the form of particles in the base composition of the invention. Component c, i.e., the flux, can also be in particle form, but this component can also constitute a matrix in which the other components are embedded. Furthermore, component c can also be dissolved in a solvent. This applies also to the gold or silver compounds, which can be used if desired in components b or d, as the case may be.

The base composition in particulate form is preferably in the form of powder, the particles being able to have a regular (e.g., spherical) and/or an irregular structure (chips, flakes etc.). The particle size of the components is preferably between about 10 and 200 $\mu$m, especially between about 20 and 60 $\mu$m. For example, the components have the following particle sizes (in $\mu$m): a 20 to 50, b 30 to 200, preferably less than 150, c less than 150, d 20 to 200, preferably less than 50, e 20 to 150, and f less than 50.

Preferably, the base composition of the invention is made up approximately of the following components (in percent by weight):
a 10 to 70, b 10 to 65, c 5 to 50, d 0.6 to 20, e 0 to 20, f 0 to 12.

An especially preferred composition (in percent by weight) is as follows:
a 20 to 50, especially 35, b 35 to 50, especially 42, c 15 to 30, especially 21, d 1.5 to 2, especially 1.8, e 0 to 20, f 0 to 8.

Preferably, the component a in the base composition contains nickel, cobalt, chromium or mixtures thereof. Such high-melting metals and alloys are known in themselves and commonly also contain amounts of Mo, Al, Si, Mn and Fe to provide properties which are advantageous for the particular application. An alloy composition for component a (in wt.-%) is as follows:
Cr 10 to 20, Mo 1 to 7, Al 1 to 5, Si 0.5 to 2, Mn 2 to 5, Fe 0 to 5, Co 0.1 to 1, balance Ni.

Within these ranges a preferred component a has the following composition in wt.-%:
Cr 17, Mo 5, Al 4, Si 1, Mn 3, Fe 0.5, Co 0.5, Ni 69.

The preferentially used alloy component a consists of irregularly shaped chips of a length of about 50 to 150 $\mu$m and a thickness of about 20 to 60 $\mu$m. Within the above-given range, component a is used within an especially selected range of approximately 20 and 40% by weight.

Component b can consist of gold or a gold alloy, the gold content of the alloy amounting to at least 50% by weight. Other alloy components can be Ag, Cu, Pt and Pd. Usually the component b will have the following composition in weight-percent:
Au 50 to 100, Ag 0 to 25, Cu 0 to 15, Pt 0 to 10, Pd 0 to 10.

A preferred composition is as follows (in weight-percent):
Au 89,4 Ag 1,6, Cu 8, Pt 0.4, Pd 0.6.

The particle size of these alloys is commonly between about 30 and 200 $\mu$m. Preferably chips are used.

The known fluxes can be used as component c. They are, for example, boric oxide, the alkali metal borates, carbonates, fluorides, fluoroborates and chlorides, especially of sodium and potassium. Basically those fluxes are preferred which remove the oxides at the surface of the metal substrate during the sintering process. Borax and sodium fluoroborate are named as preferred compounds. Within the above-named ranges, the component c can be used especially within a range of about 10 to 20% by weight.

Component d has a melting point of less than 1000° C., the melting point being further reduced by using Al-Ag alloys.

The optionally used component e is preferably an $SiO_2$ powder having a particle size of less than 50 $\mu$m. However, dental porcelains can be used instead of the pure $SiO_2$ component, but they are to contain $SiO_2$ in relatively great amounts. The $SiO_2$ content of these dental porcelains should amount to at least 40% by weight.

The use of component f is also optional, in which case the particle size should amount to less than 50 $\mu$m.

A preferred composition of the sinterable base composition is as follows:
Component a 35 weight-% of the nonprecious metal alloy named above as an example,
Component b 42 weight-% of the gold alloy named above as an example,
Component c 21 weight-% of borax
Component d 2 weight-% of aluminum powder.

At least a portion of the components of the base composition of the invention can be suspended in a liquid vehicle and marketed in this form. The base composition, however, can also be mixed with the liquid vehicle immediately before use.

The powdered base composition preferably in the form of a suspension in the liquid vehicle A, is applied to the metal substrate. This is accomplished generally by brushing, but also by dipping, spraying etc. The liquid vehicle can be an inorganic or preferably organic liquid, and should preferably be one that at least partially dissolves the flux c. The preferred liquid vehicle A is water or a mixture of glycerol and ethanol, especially in a weight ratio of approximately 1:1.

The powdered base composition can be mixed with water or the mixture of glycerol and ethanol so as to form a cream-like suspension. This can be applied to the high-melting dental metal alloy, which is in the form of a crown, for example, in a coating thickness of about 0.2 to 0.5 mm. The crown thus coated is slowly dried in a firing kiln before the coating is sintered, preferably in vacuum. The sintering is performed at rising temperatures, the rate of temperature rise being able to amount to, for example, 60° to 500° C. per minute, preferably about 120° C. per minute. The end temperature is about 800° to 1200° C., preferably about 950° C. After sintering for about two minutes, the vacuum in the kiln is broken, the kiln is opened, and the crown is removed and is allowed to cool at room temperature.

Before the firing of the dental porcelain begins, the sintered intermediate coating is treated with a liquid B in which the nonmetallic components of the base composition, especially the flux, are at least partially soluble.

The treatment liquid B is preferably a dilute mineral acid or a mixture of dilute mineral acids. The dilute mineral acid can contain about 5 to 10% of HCl and/or 5 to 10% of HF in aqueous solution. For the purpose of an especially careful cleaning of the surface of the applied coating, the treatment with liquid B can be performed in an ultrasonic bath. The nonmetallic components at the surface, i.e., especially the flux c and the metal oxides dissolved by the flux, are removed by the acid. A very rough surface is obtained, which is covered with a very thin layer of gold.

The process can probably be explained by stating that the flux (together with the silica if used) dissolves the oxides on the metal surface during the sintering process, so that component d can reach component a on the one hand and the high-melting dental metal alloy of the substrate on the other, so that first a thin adhesive primer layer of aluminum or silver forms, on which a thin gold layer spreads itself. The propagation of this gold layer is facilitated to a certain degree by the $ZrO_2$ when the latter is used. The particles of components a are therefore bound by means of the thin gold layer from component b with the dental metal alloy of the substrate. The necessary mechanical retention for the dental porcelain is provided by the surface roughness of the sintered material. By the treatment with liquid B, not only the nonmetallic components, such as the flux, are removed, but also any metal particles embedded in the flux which have shared only incompletely in the sintering process.

The high-melting dental metal alloy that is preferred for the substrate is an alloy containing nickel, cobalt and/or chromium or mixtures thereof as the chief components, whose coefficient of thermal expansion is matched to that of porcelain. In general, this alloy has approximately the same composition as component a of the base composition of the invention.

A high-melting dental metal alloy preferably used for the substrate (or for component a as the case may be) has approximately the following composition in wt.-%: Ni and/or Co 60 to 85, Cr 11 to 32, Fe 0.2 to 0.6, Al 0 to 5, Mo 1.5 to 6, Si 0 to 1.2, Be 0 to 1.6, Cu 0 to 0.2, Mg 0 to 3.5.

EXAMPLES

The invention will be explained nonrestrictively with the aid of the following examples. The following components were used:

a Nonprecious metal alloys (also suitable for substrates)

|   | Ni | Cr | Fe | Al | Mo | Si | Be | Cu | Mn | Co |
|---|---|---|---|---|---|---|---|---|---|---|
| 1. | 69 | 17 | 0.5 | 4 | 5 | 1 | — | — | 3 | 0.5 |
| 2. | 81 | 12 | 0.2 | 3 | 1.9 | 0.2 | 1.5 | 0.1 | 0.1 | — |
| 3. | 0.3 | 31.6 | 0.6 | 0.01 | 4.4 | 1 | — | 0.01 | 0.78 | 61.3 |

The alloys specified above are commercially obtainable under the trademark names Wiron S. (1), Gemini II (2) and Vitallium (3).

b Noble-metal alloys

|   | Au | Pd | Pt | Ag | Other |
|---|---|---|---|---|---|
| 1. | 87.5 | 6 | 4.5 | — | 2 |
| 2. | 89,4 | 0,6 | 0,4 | 1,6 | — | c Borax powder
d Aluminum powder

| e | Silica powder finer than 50 μm | Optional |
|---|---|---|
| f | Zirconia powder finer than 50 μm | |

A number of different sinterable base compositions were prepared, compositions A to G being prepared with the use of the components a1 to a3, b1, b2 and d specified in the tables given below. In preparing the base compositions H to M, fine gold and other gold alloys were used instead of components b1 and b2, while instead of the alumina powder (component d), an Al-Ag alloy was used in the case of base compositions H to L. The components used are given in the following table.

| base composition | Components | | | | | | | | |
|---|---|---|---|---|---|---|---|---|---|
|   | a1 | a2 | a3 | b1 | b2 | c | d | e | f |
| A | 35 |    |    | 42 |    | 21 | 1.8 | 0.2 | — |
| B |    | 35 |    |    | 35 | 25 | 5 | — | — |
| C |    |    | 35 | 35 |    | 15 | 15 | — | — |
| D | 10 |    |    |    | 40 | 20 | 10 | 8 | 12 |
| E | 35 |    |    |    | 35 | 15 | 5 | 10 | — |
| F |    | 33 |    |    | 22 | 20 | 10 | 15 | — |
| G |    |    | 32 |    | 38 | 15 | 8 | — | 7 |
|   |    |    |    | Au | Ag | Cu |    | Al | Ag |
| H | 28.69 |  |  | 39.15 | 2.0 | — | 10.65 | — | — | 10.97 | 8.57 |
| I | 35.47 |  |  | 18.14 | 0.96 | — | 15.83 | 2.44 | 0.43 | 20.37 | 6.36 |
| J | 38.74 |  |  | 27.15 | 5.09 | 1.7 | 17.25 | 2.66 | 0.47 | — | 6.94 |
| K | 46.13 |  |  | 19.95 | 1.05 | — | 13.05 | 2.66 | 0.47 | 16.69 | — |
| L | 43.92 |  |  | 24.03 | 3.4 | 1.13 | 22.18 | 4.54 | 0.8 | — | — |
| M | 39.0 |  |  | 38.0 | — | — | 20.0 | 3.0 | — | — | — |

These base compositions were mixed in each case with a vehicle (water or glycerol and ethanol 1:1) to a creamy consistency. The base compositions were applied with a brush as evenly as possible in a thickness of approximately 0.4 mm to metal plates made of the alloy composition a1 (dimensions 15×7×0.5 mm). Then the base composition was thoroughly dried and sintered in a firing kiln under vacuum at 950° C. for two minutes. The fired metal plates were cooled and then treated for 10 minutes in an ultrasonic bath with an acid solution (5% HCl) in water.

After removal from the ultrasonic bath and thorough rinsing in water, a dental porcelain layer 1.5 mm thick was fired on. The metal plates with the dental porcelain were bent to form a ring with a circumference of 15 mm and then flattened back to their original shape. After straightening, the dental porcelain on the metal plates was subjected to a strong air blast to remove any loose porcelain. The plates were then examined under a microscope. In the case of the base compositions A to M of the invention, it was found that a coat of dental porcelain was still adhering to the metal.

For comparison, dental porcelain was fired in the same manner onto alloy a1, without first sintering any base composition of the invention thereon. When the metal plate thus obtained was bent and straightened in the same manner, most of the dental porcelain spalled off, or failed to adhere at all.

What is claimed is:

1. A process for preparing and intermediate layer between a high-melting dental metal alloy and a dental porcelain which comprises applying to said high-melting dental metal alloy, a composition comprising the components:
   (a) at least a metal or a metal alloy which is thermally stable at a temperature of at least 800° C.;
   (b) gold or a gold compound which decomposes to metallic gold, or a gold alloy;
   (c) at least one flux; and
   (d) aluminum and/or silver or an aluminum—silver alloy or a silver compound which decomposes two metallic silver, in a liquid vehicle (A) in which component (c) is at least partially soluble, drying the so-treated high-melting dental metal alloy and sintering said composition and thereafter treating the so-sintered composition with a liquid (B) in which the non-metallic components of said composition are at least partially soluble.

2. A method according to claim 1, wherein said liquid vehicle (A) comprises water or a mixture of glycerol and ethanol.

3. A method according to claim 2, wherein the weight ratio between glycerol and ethanol in the liquid vehicle (A) amounts to approximately 1:1.

4. A method according to claim 1, wherein a liquid (B) comprises a dilute mineral acid or a mixture of dilute mineral acids.

5. A method according to claim 4, wherein said acid or mixture of acids comprises 5–10% HCl and/or 5–10% HF in aqueous solution.

6. A method according to claim 1, wherein the suspension of said composition is applied to said dental metal alloy such as to form a coating thereon of thickness of about 0.2 to about 0.5 mm and said composition is sintered at rising temperatures up to about 800° to 1200° C.

7. A process according to claim 6, wherein after said composition has been sintered and treated with said liquid (B) a dental porcelain is applied to said sintered layer and fired thereon.

8. A method according to claim 7, wherein the high-melting dental metal alloy and/or the metal component (a) has a thermal expansion coefficient matched to that of said dental porcelain.

9. A method according to claim 8, wherein component (a) is in the form of a metal alloy.

10. A method according to claim 9, wherein said high-melting dental metal alloy or said component (a) alloy is an alloy comprising nickel, cobalt or chromium or mixtures thereof as principal components.

11. A method according to claim 10, wherein said high-melting dental metal alloy and/or metal alloy of component (a) has the following composition, in terms of percentages by weight: Ni and/or Co 60 to 85; Cr 11 to 32; Fe 0.2 to 0.6; Al 0 to 5; Mo 1.5 to 6; Si 0 to 1.2; Be 0 to 1.6; Cu 0 to 0.2; Mg 0 to 3.5.

* * * * *